United States Patent [19]

Sato

[11] Patent Number: 4,675,017
[45] Date of Patent: Jun. 23, 1987

[54] VENTILATING NEEDLE AND METHOD OF MANUFACTURING THE SAME

[75] Inventor: Isao Sato, Yamanashi, Japan

[73] Assignee: Terumo Kabushiki Kaisha trading as Terumo Corporation, Tokyo, Japan

[21] Appl. No.: 836,480

[22] Filed: Mar. 5, 1986

[30] Foreign Application Priority Data

Mar. 11, 1985 [JP] Japan ................... 60-47776

[51] Int. Cl.$^4$ ................. A61M 5/00; B01D 46/00
[52] U.S. Cl. .................... 604/405; 210/446; 604/126; 604/411
[58] Field of Search ........... 210/433.2, 446, 450; 55/159; 604/405, 411–414, 190, 126

[56] References Cited

U.S. PATENT DOCUMENTS

| | | | |
|---|---|---|---|
| 3,157,481 | 11/1964 | Bujan | 604/190 X |
| 4,113,627 | 9/1978 | Leason | 210/446 |
| 4,298,358 | 11/1981 | Ruschke | 604/126 X |
| 4,473,094 | 9/1984 | Harris | 137/846 X |

FOREIGN PATENT DOCUMENTS 0045605 2/1982 European Pat. Off. .
2103590 2/1983 United Kingdom .

*Primary Examiner*—Dalton L. Truluck
*Attorney, Agent, or Firm*—Burns, Doane, Swecker & Mathis

[57] ABSTRACT

This invention discloses a ventilating needle having a membrane-type filter stretched across the communication passage of a hub portion of the needle. In this invention, the membrane-type filter is of 2-ply type composed of a reinforcement layer and a water-repellent filter having a higher melting point than said reinforcement layer. This membrane-type filter is thermally adhered to a step portion formed in the inner wall of the hub portion through interfusion of the reinforcement layer and the step portion. This invention also discloses a method of assembling the ventilating needle in which a membrane-type filter is adhered to a step portion formed in the inner wall of the hub by means of ultrasonic waves.

5 Claims, 7 Drawing Figures

VENTILATING NEEDLE AND METHOD OF MANUFACTURING THE SAME

BACKGROUND OF THE INVENTION (a) Field of the Invention

This invention relates to a ventilating needle required for application to a liquid or blood transfusing system or a connector assembly and, also to the method of manufacturing said ventilating needle.

(b) Description of the Prior Art

Referring to a liquid or blood transfusing system or a connector assembly, the withdrawal of a medical solution, for example, from a bottle, has hitherto been carried out by piercing a ventilating needle through the stopper of the medical solution bottle and introducing air streams into the medical solution bottle through said ventilating needle. In this case, the ventilating needle is generally fitted with a filter in order to prevent dust and other foreign matter from entering said ventilating needle from the outside. The various processes proposed to date to meet this requirement involve a means of forcing a rounded mass of fine fibers like those of, for example, purified cotton into the hub section of the ventilating needle, or embedding a sintered mass of for example, polyethylene in said hub section. This is the so-called depth type filter. The second main process is the so-called screen type filter disclosed, for example, in the Utility Model Publication No. 58-92946 which is constructed by fixing a filter composed of, for example, a membrane to the hub section of the ventilating needle by means of a cap or holder.

The depth type filter has drawbacks in that it tends to have dense and loose sections, it is insufficiently resistant to hydraulic pressure, it is unsatisfactory in terms of ventilation, and it is insufficiently able to remove bacteria.

The screen type filter has merits in that the ventilation pores can have a relatively uniform size, which permit better waterproofing and ventilating. Nevertheless, said screen type filter has drawbacks in that it is fitted to an extra member such as a cap or inserted into the needle hub section by means of a holder; air contaminated with dust and other foreign matter can pass between the filter and the hub. This makes the ventilating needle complex in structure, relatively difficult to assemble, and expensive.

SUMMARY OF THE INVENTION

This invention has been accomplished in view of the above-mentioned circumstances and is intended to provide a ventilating needle which is improved in the bactericidal effect, while sustaining the characteristics of the screen type filter, has a uniform quality, and ensures easy and inexpensive manufacture.

To attain the above-mentioned object, this invention provides a ventilating needle which comprises:
  an extremely narrow cylindrical needle-like piercing member;
  a hub holding a proximal portion of said piercing member at one end and provided with an opening at the other end for communication with said piercing member; and
  a membrane type filter stretched across the passage of said hub and wherein said filter is a 2-ply type at least at its periphery, namely, is formed of a reinforcing layer (or fusible layer) and a water-repellent layer having a higher melting point than said reinforcement layer; the water-repellent filter is stretched toward said piercing member; said reinforcing layer is prepared from a material thermally fusible with said hub; the annular stepped portion facing the opening of said hub passage and said reinforcement layer are thermally fused together all along the periphery through the narrow orifices of said water-repellent filter.

Further, the present invention provides a method of manufacturing a ventilating needle which comprises the steps of:
  forming a hub which is prepared from thermoplastic resin and is provided with a narrow hollow cylindrical needle-like piercing member at one end and an opening communicating with said piercing member at the other end;
  forming an annular stepped portion facing said opening in the inner wall of said communication passage of the hub;
  mounting a 2-ply (at least at its periphery) filter composed of a reinforcement layer (or fusible layer) prepared from material thermally fusible with said hub and a water-repellent layer having a higher melting point than said reinforcement layer on said annular stepped portion with said water-repellent filter made to face said piercing member;
  pressing together said filter and annular stepped portion;
  heating both said 2-ply filter and annular stepped portion at such a temperature as causes said reinforcement layer and annular stepped portion to be fused together, but suppresses the fusion of said water-repellent filter, thereby partly melting said annular stepped portion and forming narrow orifices in the water-repellent filter; and
  thermally fusing together said reinforcement layer and annular stepped portion all along the periphery.

The ventilating needle embodying this invention is constructed by inserting a 2-ply filter composed of a water-repellent layer and reinforcement layer into the hub opening of the ventilating needle with said water-repellent filter made to face a cannula, preparing both reinforcement layer and hub from thermally fusible material, and causing said reinforcement layer and hub to be directly fused together through the fine meshes of said water-repellent filter. Therefore, the ventilating needle of the present invention offers the advantages that the filter is improved in resistance to hydraulic pressure; the intrusion of dirt and sundry fungi from the external atmosphere is more effectively prevented; the filter mounted on the annular stepped portion of the hub opening has its periphery thermally pressed downward; a far smaller number of parts can suffice than the conventional screen type ventilating needle; and the simplified manufacturing steps enable a ventilating needle to be manufacturing with high reproducibility.

DETAILED DESCRIPTION OF THE PREFERRED EMBODIMENTS

Description may now be made with reference to the accompanying drawings of a ventilating needle embodying this invention.

Figure 1:
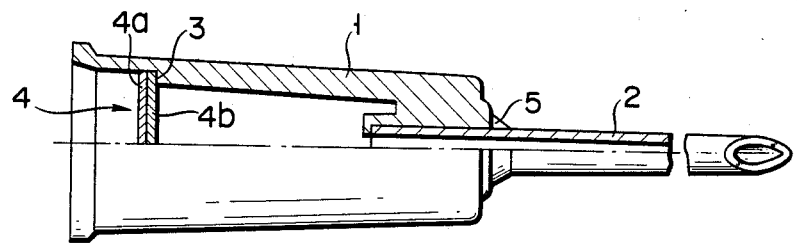
FIG. 1 is a fractional lengthwise sectional view of a ventilating needle embodying this invention.

FIG. 1 illustrates a ventilating needle embodying this invention. A proximal end of cannula 2 is fixed to the distal end of hub 1 prepared from polypropylene by injection molding by means of, for example, adhesive 5 of the epoxy series. This invention is not limited to this type, but may be constructed by integrally molding the piercing section and proximal portion by using a plastics material. The proximal end of hub 1 is left open. Annular stepped portion 3 is formed all along that portion of the inner wall which lies close to the opening of the hub 1. Membrane filter 4 is fused to the whole other peripheral edge of said annular stepped portion 3. Said filter 4 is a 2-ply type laminate manufactured, for example, by Gore Tex Co. Inc. under the trademark "Gore Tex ® laminate No. L10431". Said 2-ply laminate is composed of unwoven reinforcement layer 4a prepared from polypropylene with a thickness of 100 microns and water-repellent filter 4b prepared from polytetrafluoroethylene with a thickness of 100 microns and bearing numerous extremely fine orifices having an average diameter of 1 micron (An average of 100 orifices. When the orifice is of an ellipse, the diameter is determined by dividing the total of major and minor diameters by 2). Water-repellent filter 4b faces the aforementioned cannula. As later described, reinforcement layer 4a is securely set in place by being bonded with the annular fused portion which has been formed by penetrating extremely fine orifices 4c (FIG. 5) of water-repellent filter 4b.

Figure 2:
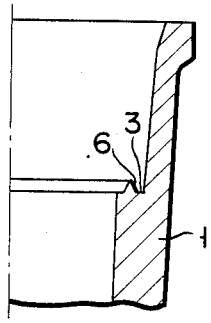
FIG. 2 is an enlarged fractional sectional view of the ventilating needle of FIG. 1.

Description may now be made of the concrete step of fusing water-repellent filter 4b to the inner wall of hub 1. First as illustrated in FIG. 2, stepped portion 3 is formed close to the hub opening so as to face it. Annular rib or projection 6 is formed along annular stepped portion 3. Said annular rib 6 has a triangular cross section whose base measures 0.3 mm and whose height indicates 0.3 mm.

Figure 3:
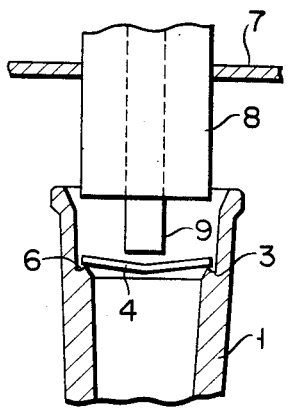
FIGS. 3, 4, 6 and 7 are sectional views showing the sequential steps of manufacturing the subject ventilating needle.

Later as seen from FIG. 3, filter sheet 7 is so set as to face the opening of hub 1 or positioned nearby. Filter 4 having a prescribed circular form corresponding to the size of annular stepped portion 3, namely, having a diameter of, for example, 4.6 mm is cut out of said sheet 7 by means of punch 8. Filter sheet 7 thus punched out is inserted into the opening of hub 1. Pin 9 projectibly held in punch 8 is pushed outward to place filter 4 on annular rib 6 constituting stepped portion 3.

Figure 6:
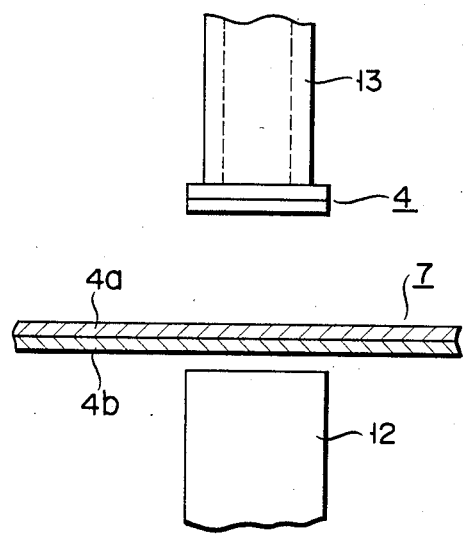
Figure 7:
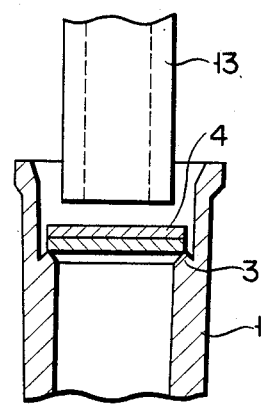

Description may now be made with reference to FIG. 6 of another process of fusing filter 4b to the inner wall of hub 1. 2-ply filter sheet 7 composed of unwoven polypropylene fabric 4a and polytetrafluoroethylene film 4b is cut out by punch 12 to provide filter 4 having a predetermined shape. Said cut out 2-ply sheet 7 is sucked by sucking pipe 13 maintained at a negative pressure. While being thus sucked, said 2-ply sheet 7 is carried into hub 1. At this time, pressurized air streams are momentarily blown into sucking pipe 13, thereby mounting filter 4 on annular rib 6.

Figure 4:
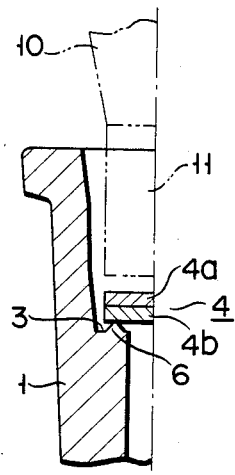

Thereafter as illustrated in FIG. 4, vibrator 11 of ultrasonic fusion apparatus 10 (the lower end of said vibrator 11 is slightly wider than the diameter for example, 4.2 mm of annular rib 6 and the other diameter of said vibrator 11 is narrower than the inner diameter for example, 4.8 mm of hub 1) is taken into the opening of hub 1. Annular rib 6 of stepped portion 3 is thermally melted by ultrasonic wares, thereby fusing the peripheral portion of circular filter 4 to annular stepped portion 3 of hub 1.

At this time heating should preferably be applied to such extent as can melt annular rib 6 and reinforcement layer 4a, but not water-repellent filter 4b. Where annular rib 6 and reinforcement layer 4a are prepared from polypropylene (melting point 164° to 170° C.) and water-repellent filter 46 is composed of polytetrafluoroethylene (melting point 327° C.), heating should preferably be applied within the range of 200° to 300° C.

During the above-mentioned heating step, circular filter 4 is forced toward annular stepped portion 3 by means of ultrasonic vibrator 11. Obviously, pressure may be applied by any other means than ultrasonic vibrator 11.

Figure 5:
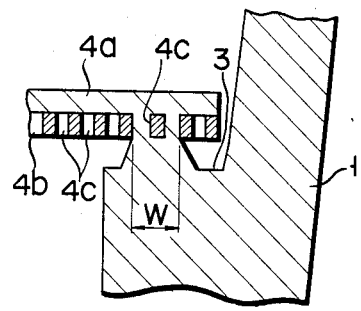
FIG. 5 is an enlarged sectional view of that portion of the subject ventilating needle with which a filter is fused.

FIG. 5 schematically shows the fused state of circular filter 4 obtained by the aforementioned process. Since ultrasonic waves have a prominent directionality, annular rib 6 mounted on stepped portion 3 is immediately melted by ultrasonic waves. The melted mass now undergoing great pressure passes through the fine orifices 4c of water-repellent filter 4 and is mixed with reinforcement layer 4a also remaining in the fused state. As a result, reinforcement layer 4a is securely fixed to the surface of annular stepped portion. At this time, it is preferred that reinforcement layer 4a be fixed to the surface of annular stepped portion 3 with a cross section measuring 0.1~1 mm in width W. It is also demanded that heating and pressure be applied to an extent adapted to the materials used in order to meet the above-mentioned requirements.

While the application of the above-mentioned ultrasonic wave filter-fusing process is indeed advisable, said process may be replaced by any other means. Namely, circular filter 4 is fitted to annular stepped portion 3 formed inside the opening of hub 1 by any other heating means. Water-repellent filter 4b and reinforcement layer 4a may be prepared from not only the aforementioned materials but also any other properly selected ones. However, it should be noted that the hub and reinforcement layer should be composed of mutually fusible materials; and water-repellent filter 4b should be prepared from such material as is infusible under the condition in which reinforcement layer 4a is thermally adhered on the inner wall of hub 1. The preferred combinations of the reinforcement layer and water-repellent filter may be listed as follows:

polypropylene—teflon
polyethylene—teflon
polycarbonate—teflon
polyvinylchloride—teflon
polypropylene—nylon
polypropylene—polyvinylidene fluoride The pore diameter of the water-repellent filter should be preferably 0.1~5 μm, more preferably 0.2~3 μm.

What is claimed is:

1. A ventilating needle which comprises:
   a hollow tubular piercing section;
   a hub holding a proximal end of said piercing section at one end, and provided with an opening communicating with said piercing section at the other end; and a membrane-type filter stretched across the communication passage of said hub, and wherein said filter is of a 2-ply type, at least at its periphery, composed of a fusible layer and a water-repellent filter having fine orifeces and a higher melting point than said fusible layer; said water-repellent filter is provided over an annular stepped portion formed all along the inner peripheral wall of the communication passage of the hub and on the side of the piercing section so as to face said piercing section; said fusible layer is prepared from a material thermally fusible with said hub; and the annular stepped portion facing the opening of said hub and the fusible layer are fused together all along the periphery through the fine orifices of said water-repellent filter.

2. The ventilating needle according to claim 1, wherein said fusible layer is composed of unwoven thermally fusible fabric.

3. The ventilating needle according to claim 2, wherein said fusible layer is selected from the group consisting of unwoven fabric prepared from polypropylene, unwoven fabric prepared from polyethylene, unwoven fabric prepared from polycarbonate, and unwoven fabric prepared from polyvinylchloride; and said water-repellent filter is prepared from tetrafluoroethylene.

4. The ventilating needle according to claim 1, wherein a fused portion of said fusible layer of the filter which is fused with said annular stepped portion has width of 0.1 mm to 1 mm.

5. The ventilating needle according to claim 1, wherein the water-repellent filter has an average diameter of 1 micron.

* * * * *

UNITED STATES PATENT AND TRADEMARK OFFICE
CERTIFICATE OF CORRECTION

PATENT NO. : 4,675,017
DATED     : June 23, 1987
INVENTOR(S) : Isao Sato

It is certified that error appears in the above-identified patent and that said Letters Patent is hereby corrected as shown below:

In column 5, line 6, amend "orifeces" to --orifices--.

Signed and Sealed this

Sixteenth Day of February, 1988

*Attest:*

DONALD J. QUIGG

*Attesting Officer*   *Commissioner of Patents and Trademarks*